US00PP12585P2

(12) United States Plant Patent
Demel

(10) Patent No.: US PP12,585 P2
(45) Date of Patent: Apr. 30, 2002

(54) SATUREJA PLANT NAMED 'INDIAN MINT'

(75) Inventor: Helmut Demel, Quedlinburg (DE)

(73) Assignee: Hishtil-Afula (1989) Ltd., IL-Afula (IL)

( * ) Notice: Subject to any disclaimer, the term of this patent is extended or adjusted under 35 U.S.C. 154(b) by 0 days.

(21) Appl. No.: 09/761,472

(22) Filed: Jan. 18, 2001

(51) Int. Cl.[7] ..... A01H 5/00
(52) U.S. Cl. ..... Plt./263
(58) Field of Search ..... Plt./263, 226, 373

(56) References Cited

PUBLICATIONS

UPOV ROM GTITM Computer Database, GTI JOUVE Retrieval Software 2001/01, citations for 'Indian Mint', 2001.*

* cited by examiner

*Primary Examiner*—Bruce R. Campell
*Assistant Examiner*—Wendy A Baker
(74) *Attorney, Agent, or Firm*—C. A. Whealy

(57) ABSTRACT

A distinct cultivar of Satureja plant named 'Indian Mint', characterized by its cascading, trailing and uniform plant habit; freely branching habit, dense and bushy growth habit; and dark green and aromatic leaves.

1 Drawing Sheet

BACKGROUND OF THE INVENTION

The present Invention relates to a new and distinct cultivar of Satureja plant, botanically known as *Satureja Douglasii*, and hereinafter referred to by the name 'Indian Mint'.

The new cultivar is a product of a planned breeding program conducted by the Inventor in Quedlinburg, Germany. The new Satureja originated from a cross of a proprietary Satureja selection identified as KA, not patented, as the female, or seed, parent with a proprietary Satureja selection identified as KB/95, not patented, as the male, or pollen, parent. The new Satureja was selected by the Inventor in 1996 on the basis of its cascading, trailing and uniform plant habit. The new Satureja differs from the parental selections primarily in plant habit.

Asexual reproduction of the new Satureja by terminal cuttings in a controlled environment in Quedlinburg, Germany, has shown that the unique features of this new Satureja are stable and reproduced true to type in successive generations.

SUMMARY OF THE INVENTION

Plants of the cultivar Indian Mint have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Indian Mint'. These characteristics in combination distinguish 'Indian Mint' as a new and distinct cultivar:

1. Cascading, trailing and uniform plant habit.
2. Freely branching habit, dense and bushy growth habit.
3. Dark green and aromatic leaves.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Satureja. The photograph comprises a side perspective view of a typical 5-month old plant of 'Indian Mint' grown in a hanging basket container.

DETAILED BOTANICAL DESCRIPTION

In the following description, color references are made to The Royal Horticultural Society Colour Chart except where general terms of ordinary dictionary significance are used. Plants were grown in a glass-covered greenhouse and under conditions which closely approximate commercial production conditions in Quedlinburg, Germany, during the spring and summer with minimum night temperatures of about 15° C. and under natural daylength. Plants used for this description were about 4 to 5 months old.

Botanical classification: *Satureja Douglasii* cultivar Indian Mint.

Parentage:

*Female, or seed, parent.*—Proprietary selection of *Satureja Douglasii* identified as KA, not patented.

*Male, or pollen, parent.*—Proprietary selection of *Satureja Douglasii* identified as KB/95, not patented.

Propagation:

*Type cutting.*—By terminal cuttings.

*Time to initiate and develop roots.*—About 14 to 20 days at 15° C.

*Root description.*—Fine, fibrous and well-branched.

Plant description:

*Form.*—Cascading, trailing and uniform plant habit; indeterminate. Freely branching with two lateral branches potentially forming at every node; dense and bushy growth habit.

*Plant height (soil level to top of plant plane).*—About 8 cm.

*Plant diameter or spread.*—About 50 cm.

*Plant length.*—About 2.5 meters.

*Lateral branches.*—Length: About 25 to 100 cm. Diameter: About 1 mm; square in cross-section. Internode length: About 9 mm to 2.9 cm. Texture: Short, fine and dense pubescence. Color: Close to 146D, occasionally some anthocyanin, close to 200D.

*Foliage description.*—Simple, opposite. Length: About 2 cm. Width: About 1.9 cm. Shape: Deltoid to rounded with cordate tendencies. Apex: Obtuse. Base: Truncate. Margin: Crenate. Aspect: Slightly cupped. Texture: Slightly rugose; very short and sparse pubescence. Fragrance: Very aromatic, mint-like. Color: Young leaves, upper surface: Close to 144A. Young leaves, lower surface: Close to 147C. Fully developed leaves, upper surface: Close to 147A to close to 139B; venation, close to 147C. Fully developed leaves, lower surface: Close to 147B; venation, close to 147C. Petiole: Length: About 6 mm. Diameter: About 0.9 mm. Color: Close to 147C.

Flower description:

*Flower arrangement and shape.*—Small single labiate flowers arranged in leaf axils; one flower per leaf axil; small and very inconspicuous.

*Natural flowering season.*—During the summer, flowering continuous.

*Flower longevity on the plant.*—Longevity of individual flowers is highly dependent on weather conditions, typically about one to two weeks. Flowers persistent.

*Flower diameter.*—Very small, about 6.5 mm.

*Petals.*—Arrangement: Five in a single whorl; fused. Color: Upper petal, white, lighter than 155D; lower four petals, very light pink, close to 69D.

*Seed.*—Seed development has not been observed.

Disease resistance: Plants of the new Satureja have not been noted to be resistant to pathogens common to Satureja.

Weather tolerance: Plants of the new Satureja have been observed to be tolerant to rain and wind. Plants of the new Satureja have been observed to tolerate high summer temperatures when grown in Germany, but are considered cold hardy in Germany.

It is claimed:

1. A new and distinct cultivar of Satureja plant named 'Indian Mint', as illustrated and described.

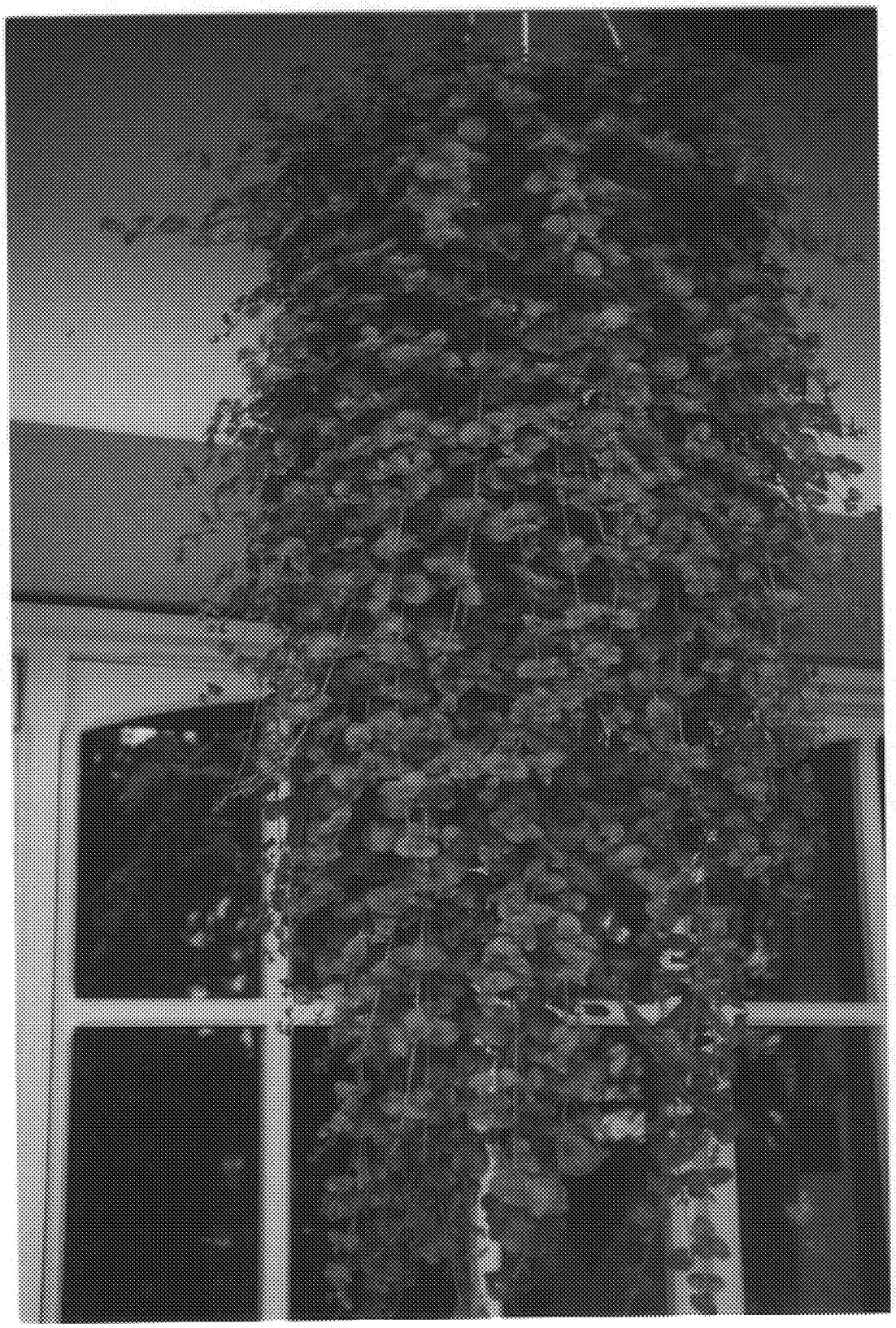

* * * * *